United States Patent
Sato et al.

[11] Patent Number: 5,475,130
[45] Date of Patent: Dec. 12, 1995

[54] ANILIDE DERIVATIVE

[75] Inventors: Masakazu Sato, Saitama; Yutaka Kawashima, Gunma; Katsuo Hatayama, Saitama, all of Japan

[73] Assignee: Taisho Pharmaceutical Co., Ltd., Tokyo, Japan

[21] Appl. No.: 64,073

[22] PCT Filed: Nov. 21, 1991

[86] PCT No.: PCT/JP91/01602

§ 371 Date: May 25, 1993

§ 102(e) Date: May 25, 1993

[87] PCT Pub. No.: WO92/09572

PCT Pub. Date: Nov. 6, 1992

[30] Foreign Application Priority Data

Nov. 26, 1990 [JP] Japan ............... 2-322136

[51] Int. Cl.$^6$ ............ C07C 327/34; C07C 323/25; C07C 323/41; A61K 31/265
[52] U.S. Cl. .............. 558/254; 564/162; 564/200; 564/218
[58] Field of Search ............... 564/162, 200, 564/218; 558/254; 514/513, 618, 625, 629, 824

[56] References Cited

U.S. PATENT DOCUMENTS

| | | | |
|---|---|---|---|
| 3,878,248 | 4/1975 | Phillips | 71/98 |
| 4,329,363 | 5/1982 | Dorn et al. | 564/162 |
| 4,623,662 | 11/1986 | De Vries | 514/596 |

FOREIGN PATENT DOCUMENTS

| | | |
|---|---|---|
| 54-39028 | 3/1979 | Japan. |
| 60-41655 | 3/1985 | Japan. |
| 62-277351 | 12/1987 | Japan. |
| 63-253060 | 10/1988 | Japan. |
| 2-157260 | 6/1990 | Japan. |

*Primary Examiner*—Richard L. Raymond
*Assistant Examiner*—B. Bembenick
*Attorney, Agent, or Firm*—Oblon, Spivak, McClelland, Maier, & Neustadt

[57] ABSTRACT

An anilide derivative useful as an atherosclerosis treating drug, represented by the following formula (I):

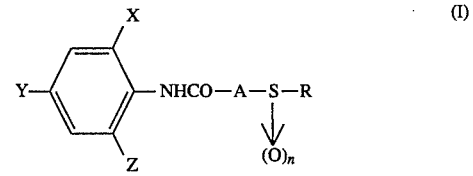

wherein X is an alkyl group having 1 to 4 carbon atoms or an alkoxy group having 1 to 4 carbon atoms; Y is a hydrogen atom or an alkoxy group having 1 to 4 carbon atoms; Z is an alkyl group having 1 to 4 carbon atoms or an alkoxy group having 1 to 4 carbon atoms; A is an alkylene group having 1 to 4 carbon atoms; R is an alkyl group having 6 to 20 carbon atoms, an alkanoyl group having 2 to 20 carbon atoms or a benzyl group which may be substituted with an alkyl group having 1 to 4 carbon atoms; and n is 0, 1 or 2.

19 Claims, No Drawings

ANILIDE DERIVATIVE

TECHNICAL FIELD

This invention relates to a compound having an activity to inhibit ACAT (acyl-coenzyme A cholesterol acyltransferase).

BACKGROUND ART

It is known that ACAT is an enzyme which catalyzes synthesis of cholesterol esters from fatty acid acyl-coenzyme A and cholesterol, and esterification of cholesterol in the living body is effected mostly by the function of ACAT (A. A. Spector et al., *Prog. Lipid Res.*, vol.18, pp.31–53 (1979)).

In addition, since increase in the ACAT activity has been found in experimentally prepared atherosclerotic lesions, a relationship between the accumulation of cholesterol esters and the ACAT activity in atherosclerotic lesions has been indicated (St. Clair et al., *Circ. Res.*, vol.27, pp.213–225 (1970); St. Clair et al., *Prog. Cardiovasc. Dis.*, vol.26, pp.109–132 (1983); P. M. Kinnuen et al., *Biochemistry*, vol.27, pp.7344–7350 (1988)).

On the other hand, with regard to the absorption of dietary cholesterol, it is known that free cholesterol in the intestinal tract is esterificated in the small intestine mucous membrane and then secreted as chylomicron into the lymphatic duct, and ACAT located in the small intestine mucous membrane is greatly concerned in the esterification of cholesterol (K. E. Sucklinget et al., *J. Lipid Res.*, vol.26, pp.647–671 (1985); J. G. Heider et al., *J. Lipid Res.*, vol.34, pp.176–183 (1983)).

Thus, it seems that an ACAT inhibitor can inhibit formation and progress of atherosclerosis by inhibiting accumulation of cholesterol esters in atherosclerotic lesions and also can inhibit absorption of cholesterol in the small intestine mucous membrane.

Examples of prior art ACAT inhibitors include substituted urea derivatives disclosed in U.S. Pat. No. 4,623,662 and anilide derivatives disclosed in JP-A-60-41655 and JP-A-63-253060, though their functions are not sufficient enough.

Though compounds similar to the compound of the present invention have been disclosed in JP-A-54-39028 and U.S. Pat. No. 3,878,248, they have no strong ACAT inhibiting activities.

A primary object of the present invention is to provide a compound having a potent ACAT inhibiting activity.

DISCLOSURE OF THE INVENTION

The present invention relates to an anilide derivative represented by the following formula (I):

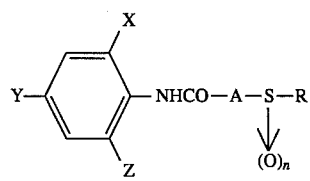

wherein X is an alkyl group having 1 to 4 carbon atoms or an alkoxy group having 1 to 4 carbon atoms; Y is a hydrogen atom or an alkoxy group having 1 to 4 carbon atoms; Z is an alkyl group having 1 to 4 carbon atoms or an alkoxy group having 1 to 4 carbon atoms; A is an alkylene group having 1 to 4 carbon atoms; R is an alkyl group having 6 to 20 carbon atoms, an alkanoyl group having 2 to 20 carbon atoms or a benzyl group which may be substituted with an alkyl group having 1 to 4 carbon atoms; and n is 0, 1 or 2.

The alkyl group according to the present invention is a straight- or branched-chain alkyl group, and the alkyl groups represented by X and Z include, for example, methyl, ethyl, propyl, isopropyl, butyl, isobutyl, t-butyl and the like groups, and those represented by R include octyl, decyl, dodecyl, tetradecyl, pentadecyl, eicosanyl and the like groups. Preferably, the alkyl group represented by X is an isopropyl group, and the alkyl group represented by R is an alkyl group having 8 to 16 carbon atoms. The alkoxy group disclosed herein is a straight- or branched-chain alkoxy group such as methoxy, ethoxy, propoxy, isopropoxy, butoxy, isobutoxy, t-butoxy or the like group. The alkylene group is a straight- or branched-chain alkylene group such as methylene, ethylene, trimethylene, dimethylmethylene, tetramethylene or the like group.

The compound of formula I can be produced, for example, by the following process. That is, the thioester portion of an anilide derivative represented by the following formula (II):

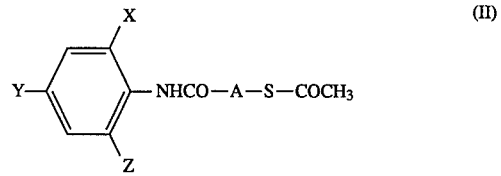

(in formula (II), X, Y, Z and A are the same as defined above) is converted into a thiol form by hydrolysis according to an ordinary ester hydrolysis technique (for example, its reaction with potassium hydroxide in water-containing ethanol), and the resulting product is allowed immediately to react with a compound represented by formula R-Hal (in this formula, R is the same as defined above, and Hal is a halogen atom), thereby obtaining a member of the compound of formula (I) in which n is 0.

Another member of the compound of formula (I), in which n is 1 or 2, may be obtained by oxidizing the compound obtained by the above process in an inert solvent. Examples of the oxidizing agent to be used include hydrogen peroxide, m-chlorobenzoic acid, peracetic acid, and the like. Examples of the inert solvent include water, acetic acid, alcohols such as methanol, ethanol, isopropyl alcohol or t-butyl alcohol, ethers such as dioxane or tetrahydrofuran, dimethylformamide, dimethylsulfoxide, methylene chloride, chloroform, acetone, and the like.

The compound of formula I can be produced also by the following process. That is, an anilide derivative represented by the following formula (III):

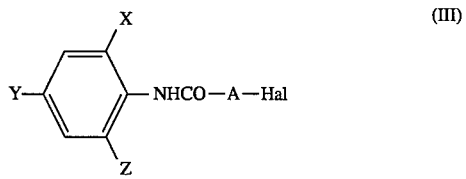

(in formula (III), X, Y, Z and A are the same as defined above, and Hal is a halogen atom) is allowed to react with a compound represented by formula R-SH (in this formula, R is the same as defined above) in the presence of a base, thereby obtaining a member of the compound of formula (I) in which n is 0.

Another member of the compound of formula (I), in which n is 1 or 2, may be obtained by oxidizing the compound obtained in the same manner as described above. Examples of the base to be used herein include inorganic bases such as potassium carbonate, sodium carbonate, sodium hydroxide or potassium hydroxide, organic bases such as triethylamine, diisopropylethylamine or pyridine, alkoxides such as sodium methoxide, sodium ethoxide or potassium t-butoxide, sodium hydride, potassium hydride, sodium amide, and the like.

The compound of formula (I) can be produced also by the following process. That is, an anilide derivative represented by the following formula (IV):

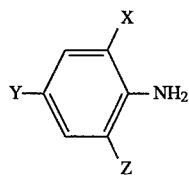

(in formula (Iv), X, Y and Z are the same as defined above) is allowed to react with a compound represented by formula R-S-A-CO-Hal (in this formula, R and A are the same as defined above, and Hal is a halogen atom) in the presence of a base, thereby obtaining a member of the compound of formula (I) in which n is 0. Any of the bases described above can be used in this reaction. Also, oxidation reaction of sulfur atom can be effected in the same manner as described above.

Preferred examples of the compound of formula I include N-(2,6-diisopropylphenyl)-2-(tetradecylthio)acetamide, N-(2,6-diisopropylphenyl)-2-(octadecylthio)acetamide, N-(2,6-diisopropylphenyl)-4-(tetradecylthio)butanamide, N-(2,6-diisopropylphenyl)-3-(tetradecylthio)propanamide and N-(2-methyl-6-t-butylphenyl)-2-(tetradecylthio)acetamide.

When the compound of formula (I) is used as a pharmaceutical preparation for the treatment of arteriosclerosis, the compound administered orally or parenterally in various dosage forms such as tablets, pills, capsules, granules, injections and the like. Each of these preparations may be produced in accordance with an ordinary formulation technique, if necessary, by adding generally used additive agents such as a filler, a binder, a buffer or a solvent.

Though dose of the compound of formula (I) may vary depending on the age of each patient, type and condition of the disease to be treated and other factors, the compound may be usually administered in a dose of 2 to 2,000 mg per day by dividing the daily dose into 1 to several times.

INDUSTRIAL APPLICABILITY

The compound of the present invention is useful as a pharmaceutical preparation for use in the treatment of arteriosclerosis, because the inventive compound shows significant activity in ACAT inhibition tests in which rabbit small intestinal microsomes are used.

BEST MODE FOR EMBODYING THE INVENTION

To further illustrate the present invention, the following Examples and Test Examples will be given.

EXAMPLE 1

Production of N-(2,6-diisopropylphenyl)-2-(tetradecylthio)acetamide (compound 1):

A mixture consisting of N-(2,6-diisopropylphenyl)-2-chloroacetamide (2.54 g), tetradecylmercaptan (2.3 g), potassium carbonate (3.6 g), sodium iodide (60 mg) and ethanol (50 ml) was subjected to 6 hours of reflux under an argon atmosphere. After removing the reaction solvent by distillation under a reduced pressure, the resulting product was mixed with ethyl acetate, washed successively with water and saturated brine and then dried on anhydrous magnesium sulfate. Thereafter, the solvent was removed by distillation under a reduced pressure, and the resulting residue was subjected to crystallization using isopropyl ether to obtain the title compound (3.14 g) in the form of colorless needle crystals.

Melting point: 62.5°–64° C.

EXAMPLE 2

Production of N-(2,6-diisopropylphenyl)-2-(octylthio)acetamide (compound 2):

To a mixture consisting of N-(2,6-diisopropylphenyl)-2-(acetylthio)acetamide (5.87 g) and ethanol (80 ml) was added dropwise 10% sodium hydroxide aqueous solution (20 ml) at 0° C. under an argon atmosphere. The reaction mixture was stirred for 30 minutes, mixed with octyl bromide (3.86 g) and then stirred again for 4 hours at room temperature. After removing the reaction solvent by distillation under a reduced pressure, the resulting residue was mixed with ethyl acetate, washed with saturated brine and then dried on anhydrous magnesium sulfate. After removing the solvent by distillation under a reduced pressure, the resulting residue was subjected to a silica gel column chromatography (developing solvent; ethyl acetate:hexane= 1:4) and then to crystallization using hexane, thereby obtaining the title compound (5.13 g) in the form of colorless needle crystals.

Melting point: 86.5°–87.5° C.

The following compounds were obtained in the same manner.

N-(2,6-diisopropylphenyl)-2-(decylthio)acetamide (compound 3):
Melting point: 70°–71° C.

N-(2,6-diisopropylphenyl)-2-(dodecylthio)acetamide (compound 4):
Melting point: 64°–66° C.

N-(2,6-diisopropylphenyl)-2-(hexadecylthio)acetamide (compound 5):
Melting point: 92.5°–93° C.

N-(2,6-diisopropylphenyl)-2-(octadecylthio)acetamide (compound 6):
Melting point: 77.5°14 78.5° C.

N-(2,6-diisopropylphenyl)-2-(eicosylthio)acetamide (compound 7):
Melting point: 105°–106° C.

N-(2,6-diisopropylphenyl)-2-(4-t-butylbenzylthio)acetamide (compound 8):
Melting point: 137.5°–138.5° C.

N-(2,6-diisopropylphenyl)-2-methyl-2-(tetradecylthio)propanamide (compound 9):
Melting point: 87.5°–89.5° C.

N-(2,6-diisopropylphenyl)-4-(tetradecylthio)butanamide (compound 10):
Melting point: 64°–67° C.

N-(2,4,6-trimethoxyphenyl)-2-(tetradecylthio)acetamide (compound 11):

Melting point: 99°–101.5° C.

EXAMPLE 3

Production of N-(2,6-diisopropylphenyl)-3-(tetradecylthio)propanamide (compound 12):

A mixture consisting of 3-(tetradecylthio)propionic acid (3.02 g) and thionyl chloride (20 ml) was stirred for 30 minutes at room temperature and then evaporated under a reduced pressure to obtain 3-(tetradecylthio)propionyl chloride. The thus obtained 3-(tetradecylthio)propionyl chloride was dissolved in toluene (5 ml) and added dropwise to a mixture consisting of 2,6-diisopropylaniline (1.77 g), triethylamine (2.1 ml) and toluene (20 ml), followed by 1 hour of stirring at room temperature. The reaction mixture was washed with 3% hydrochloric acid, 10% sodium hydroxide solution and saturated brine successively and then dried on anhydrous magnesium sulfate. After removing the solvent by distillation under a reduced pressure, the resulting residue was subjected to a silica gel column chromatography (developing solvent; ethyl acetate:hexane=1:5) and then to crystallization using isopropyl ether, thereby obtaining the title compound (2.55 g) in the form of colorless needle crystals.

Melting point: 73°–74° C.

EXAMPLE 4

Production of N-(2,6-diisopropylphenyl)-2-(tetradecylsulfenyl)acetamide (compound 13):

With cooling on an ice bath, a methylene chloride solution (20 ml) containing m-chloroperbenzoic acid (1.72 g) was added dropwise to a methylene chloride solution (100 ml) containing N-(2,6-diisopropylphenyl)-2-(tetradecylthio)acetamide (compound 1) (4.48 g). The reaction mixture was stirred for 1 hour at room temperature, washed with saturated sodiumbicarbonate aqueous solution and then dried on anhydrous magnesium sulfate. After removing the solvent by distillation under a reduced pressure, the resulting residue was subjected to a silica gel column chromatography (developing solvent; ethyl acetate:hexane=1:1), thereby obtaining the title compound (3.36 g) in the form of colorless prism crystals.

Melting point: 61°–64° C.

EXAMPLE 5

Production of N-(2,6-diisopropylphenyl)-2-(tetradecylsulfonyl)acetamide (compound 14):

With cooling on an ice bath, a methylene chloride solution (40 ml) containing m-chloroperbenzoic acid (3.45 g) was added dropwise to a methylene chloride solution (100 ml) containing N-(2,6-diisopropylphenyl)-2-(tetradecylthio)acetamide (compound 1) (4.48 g). The reaction mixture was stirred for 1 hour at room temperature, washed with saturated sodiumbicarbonate aqueous solution and then dried on anhydrous magnesium sulfate. After removing the solvent by distillation under a reduced pressure, the resulting residue was subjected to a silica gel column chromatography (developing solvent; ethyl acetate:hexane=1:4) and then to crystallization using hexane, thereby obtaining the title compound (3.84 g).

Melting point: 89.5°–92° C.

The following compounds were obtained in the same manner.

N-(2,6-diisopropylphenyl)-2-(octylsulfonyl)acetamide-(compound 15):
Melting point: 127°–132° C.

N-(2,6-diisopropylphenyl)-2-(decylsulfonyl)acetamide-(compound 16):
Melting point: 110°–115.5° C.

N-(2,6-diisopropylphenyl)-2-(dodecylsulfonyl)acetamide (compound 17):
Melting point: 100°–101° C.

N-(2,6-diisopropylphenyl)-2-(hexadecylsulfonyl)acetamide (compound 18):
Melting point: 99°–100° C.

N-(2,6-diisopropylphenyl)-2-(octadecylsulfonyl)acetamide (compound 19):
Melting point: 91.5°–93° C.

N-(2,6-diisopropylphenyl)-2-(eicosylsulfonyl)acetamide (compound 20):
Melting point: 85.5°–91° C.

EXAMPLE 6

Production of N-(2,6-diisopropylphenyl)-2-(dodecanoylthio)acetamide (compound 21):

To a mixture consisting of N-(2,6-diisopropylphenyl)-2-(acetylthio)acetamide (1.5 g) and ethanol (5 ml) was added 10% sodium hydroxide aqueous solution (2 ml) under an argon atmosphere, followed by 10 minutes of stirring at room temperature. The reaction mixture was mixed with 3% hydrochloric acid and then extracted with ether. The resulting ether layer was washed with saturated brine, dried on anhydrous magnesium sulfate and then mixed with triethylamine (0.77 ml) and dodecanoyl chloride (1.16 g), followed by 1 hour of stirring at room temperature. After removing insoluble materials from the reaction mixture by filtration, the solvent was removed by distillation under a reduced pressure, and the resulting residue was subjected to a silica gel column chromatography (developing solvent; ethyl acetate: hexane=5:1), thereby obtaining the title compound (1.77 g) in the form of colorless needle crystals.

Melting point: 100.5°–101.5° C.

The following compounds were obtained in the same manner.

N-(2,4,6-trimethoxyphenyl)-2-(dodecanoylthio)acetamide (compound 22):
Melting point: 98.5°–100° C.

N-(2-methyl-6-t-butylphenyl)-2-(acetylthio)acetamide (compound 23):
Melting point: 200°–201.5° C.

N-(2-methyl-6-t-butylphenyl)-2-(tetradecylthio)acetamide (compound 24):
Melting point: 71°–73° C.

EXAMPLE 7

Tablets were prepared by the conventional techniques known in the art in accordance with the following formulation.

| (Formulation) | |
|---|---|
| Compound 1 | 100 mg |
| Hydroxypropyl cellulose | 80 mg |
| Crystalline cellulose | 50 mg |
| Lactose | 50 mg |
| Soft silicic anhydride | 20 mg |
| Talc | 20 mg |
| Total (per one tablet) | 320 mg |

EXAMPLE 8

Capsules were prepared by the conventional techniques known in the art in accordance with the following formulation.

| (Formulation) | |
|---|---|
| Compound 10 | 100 mg |
| Crystalline cellulose | 100 mg |
| Lactose | 150 mg |
| Soft silicic anhydride | 20 mg |
| Total (per one capsule) | 370 mg |

EXAMPLE 9

Granules were prepared by the conventional techniques known in the art in accordance with the following formulation.

| (Formulation) | |
|---|---|
| Compound 6 | 200 mg |
| Lactose | 200 mg |
| Hydroxypropyl cellulose | 20 mg |
| Talc | 10 mg |
| Total (per one package) | 430 mg |

A test example is shown below.

TEST EXAMPLE (ACAT inhibition activity)

The following test was carried out in accordance with the method disclosed in *J. Lipid Res.*, vol.22, p.271 (1981).

A rabbit small intestinal microsome fraction was prepared in the usual way, and the thus prepared microsome fraction was suspended in 0.04N potassiumphosphate buffer (pH 7.4) containing 0.1N sucrose, 0.03N ethylenediaminetetraacetic acid (EDTA) and 0.05N potassium chloride. Each of the drugs to be tested was dissolved in dimethyl sulfoxide.

The rabbit small intestinal microsome fraction suspension prepared above (250 μg as protein) and [1-$^{14}$C]oleyl coenzyme A were added to 0.05N phosphate buffer (pH 7.4) containing 1% bovine serum albumin, followed by the addition of a drug to be tested with varied concentration, and the total volume was adjusted to 500 μl. The thus prepared mixture was incubated at 37° C. for 6 minutes, and the reaction was terminated by adding a mixture of chloroform and methanol (mixing ratio=2:1). After stirring, the resulting chloroform layer was collected and dried by concentration. A 30 μl portion of a cholesterol oleate chloroform solution (concentration, 10 mg/ml) was added to the thus dried sample, and the mixture was spotted on a silica gel thin layer plate (Kieser Gel Art 5715, manufactured by Merck & Co., Inc.) and developed using a mixture of hexane and ethyl acetate (mixing ratio=100:3). A gel portion corresponding to cholesterol oleate was cut out and its radioactivity was measured using a liquid scintillation counter (LSC-3000, manufactured by Aroka Co., Ltd.). Samples obtained without using the drugs to be tested were also treated and measured in the same manner. Based on these results, inhibition ratio (%) of the ACAT activity was calculated using the following equation to obtain $IC_{50}$ value.

ACAT activity inhibition ratio (%)=(A−B)/B×100

A: ACAT activity when a drug to be tested is administered.

B: ACAT activity when a drug to be tested is not admistered.

The results are shown in the following table.

TABLE

| Drug Tested | Activity | Drug Tested | Activity |
|---|---|---|---|
| Compound 1 | +++ | Compound 12 | +++ |
| Compound 4 | ++ | Compound 13 | ++ |
| Compound 5 | ++ | Compound 14 | ++ |
| Compound 6 | +++ | Compound 17 | ++ |
| Compound 8 | ++ | Compound 18 | ++ |
| Compound 9 | ++ | Compound 24 | +++ |
| Compound 10 | +++ | CL277082 | + |

(Note) Each of the symbols in the above table indicates strength of the activity as follows.

| Activity | IC50 value (nM) |
|---|---|
| + | 1000–100 |
| ++ | 100–10 |
| +++ | 10–1 |

CL277082: N-(2,4-difluorophenyl)-N-[(4-neopentylphenyl)methyl]-N-heptylurea

What is claimed is:

1. A compound represented by the following formula (I):

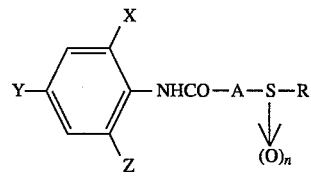

wherein X is an alkyl group having 1 to 4 carbon atoms or an alkoxy group having 1 to 4 carbon atoms; Y is a hydrogen atom or an alkoxy group having 1 to 4 carbon atoms; Z is an alkyl group having 1 to 4 carbon atoms or an alkoxy group having 1 to 4 carbon atoms; A is an alkylene group having 1 to 4 carbon atoms; R is an alkyl group having 6 to 20 carbon atoms, an alkanoyl group having 2 to 20 carbon atoms or a benzyl group which may be substituted with an alkyl group having 1 to 4 carbon atoms; and n is 0, 1 or 2.

2. The compound according to claim 1 which is N-(2,6-diisopropylphenyl)-2-(tetradecylthio)acetamide.

3. The compound according to claim 1 which is N-(2,6-diisopropylphenyl)-2-(octadecylthio)acetamide.

4. The compound according to claim 1 which is N-(2,6-diisopropylphenyl)-4-(tetradecylthio)butanamide.

5. The compound according to claim 1 which is N-(2,6-diisopropylphenyl)-3-(tetradecylthio)propanamide.

6. The compound according to claim 1 which is N-(2-methyl-6-t-butylphenyl)-2-(tetradecylthio)acetamide.

7. A method of treating arteriosclerosis, comprising the steps of:

administering to a patient in need thereof an effective amount of a compound represented by formula (I):

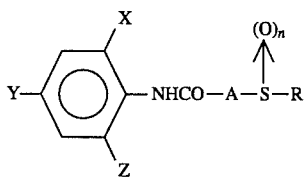

wherein X is an alkyl group having from 1–4 carbon atoms or an alkoxy group having from 1–4 carbon atoms; Y is a hydrogen atom or an alkoxy group having from 1–4 carbon atoms; Z is an alkyl group having from 1–4 carbon atoms or an alkoxy group having from 1–4 carbon atoms; A is an alkylene group having from 1–4 carbon atoms; R is an alkyl group having from 6–20 carbon atoms, an alkanoyl group having 2–20 carbon atoms or a benzyl group which may be substituted with an alkyl group having from 1–4 carbon atoms; and n is 0, 1, or 2.

8. A method of inhibiting acyl-coenzyme A cholesterol acyl transferase, comprising the steps of:

administering to a patient in need thereof an effective amount of a compound represented by formula (I):

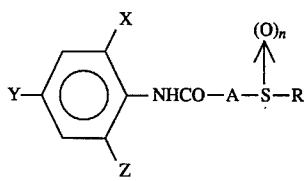

wherein X is an alkyl group having from 1–4 carbon atoms or an alkoxy group having from 1–4 carbon atoms; Y is a hydrogen atom or an alkoxy group having from 1–4 carbon atoms; Z is an alkyl group having from 1–4 carbon atoms or an alkoxy group having from 1–4 carbon atoms; A is an alkylene group having from 1–4 carbon atoms; R is an alkyl group having from 6–20 carbon atoms, an alkanoyl group having 2–20 carbon atoms or a benzyl group which may be substituted with an alkyl group having from 1–4 carbon atoms; and n is 0, 1, or 2.

9. A pharmaceutical composition, comprising:

a compound represented by formula (I):

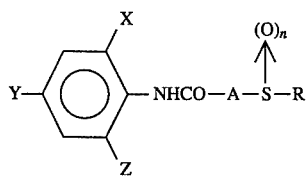

wherein X is an alkyl group having from 1–4 carbon atoms or an alkoxy group having from 1–4 carbon atoms; Y is a hydrogen atom or an alkoxy group having from 1–4 carbon atoms; Z is an alkyl group having from 1–4 carbon atoms or an alkoxy group having from 1–4 carbon atoms; A is an alkylene group having from 1–4 carbon atoms; R is an alkyl group having from 6–20 carbon atoms, an alkanoyl group having 2–20 carbon atoms or a benzyl group which may be substituted with an alkyl group having from 1–4 carbon atoms; and n is 0, 1, or 2; and a pharmaceutically acceptable excipient.

10. The method according to claim 7 wherein the compound is N-(2,6-diisopropylphenyl)-2-(tetradecylthio)acetamide.

11. The method according to claim 7 wherein the compound is N-(2,6-diisopropylphenyl)-2-(octadecylthio)acetamide.

12. The method according to claim 7 wherein the compound is N-(2,6-diisopropylphenyl)-4-(tetradecylthio)butanamide.

13. The method according to claim 7 wherein the compound is N-(2,6-diisopropylphenyl)-3-(tetradecylthio)propanamide.

14. The method according to claim 7 wherein the compound is N-(2-methyl-6-t-butylphenyl)-2-(tetradecylthio)acetamide.

15. The method according to claim 8 wherein the compound is N-(2,6-diisopropylphenyl)-2-(tetradecylthio)acetamide.

16. The method according to claim 8 wherein the compound is N-(2,6-diisopropylphenyl)-2-(octadecylthio)acetamide.

17. The method according to claim 8 wherein the compound is N-(2,6-diisopropylphenyl)-4-(tetradecylthio)butanamide.

18. The method according to claim 8 wherein the compound is N-(2,6-diisopropylphenyl)-3-(tetradecylthio)propanamide.

19. The method according to claim 8 wherein the compound is N-(2-methyl-6-t-butylphenyl)-2-(tetradecylthio)acetamide.

* * * * *

UNITED STATES PATENT AND TRADEMARK OFFICE
CERTIFICATE OF CORRECTION

PATENT NO.  : 5,475,130
DATED       : December 12, 1995
INVENTOR(S) : Masakazu SATO, et al.

It is certified that error appears in the above-indentified patent and that said Letters Patent is hereby corrected as shown below:

On the title page, Item [87] PCT should read:

--PCT Pub. No.:  WO92/09572
   PCT Pub. Date: Jun. 11, 1992--

Signed and Sealed this

Nineteenth Day of March, 1996

Attest:

BRUCE LEHMAN

*Attesting Officer*    *Commissioner of Patents and Trademarks*